(12) United States Patent
Saita et al.

(10) Patent No.: US 6,719,565 B1
(45) Date of Patent: Apr. 13, 2004

(54) HAIR COLOR ADVICE SYSTEM

(75) Inventors: Yoshimichi Saita, Tokyo (JP); Tomohito Koshika, Tokyo (JP); Manabu Yanagiya, Tokyo (JP)

(73) Assignee: Kao Corporation, Tokyo (JP)

( * ) Notice: Subject to any disclaimer, the term of this patent is extended or adjusted under 35 U.S.C. 154(b) by 97 days.

(21) Appl. No.: 09/857,215

(22) PCT Filed: Oct. 26, 2000

(86) PCT No.: PCT/JP00/07492

§ 371 (c)(1), (2), (4) Date: Jun. 22, 2001

(87) PCT Pub. No.: WO01/32051

PCT Pub. Date: May 10, 2001

(30) Foreign Application Priority Data

Oct. 29, 1999 (JP) .......... 11-310388

(51) Int. Cl.[7] .............. G09B 19/10
(52) U.S. Cl. .......... 434/94; 434/365; 434/377; 428/42.3; 702/32
(58) Field of Search .......... 434/81, 94, 98, 434/365, 377, 395; 428/42.3; 347/4, 129; 345/633, 962; 700/90; 702/32; 705/26

(56) References Cited

U.S. PATENT DOCUMENTS

| | | | |
|---|---|---|---|
| 4,434,467 A | * | 2/1984 | Scott .......... 700/90 |
| 4,872,056 A | | 10/1989 | Hicks et al. |
| 5,280,305 A | * | 1/1994 | Monroe et al. .......... 347/129 |
| 6,106,917 A | * | 8/2000 | Pereira et al. .......... 428/42.3 |
| 2002/0010556 A1 | * | 1/2002 | Marapane et al. .......... 702/32 |

FOREIGN PATENT DOCUMENTS

| | | |
|---|---|---|
| EP | 0 092 075 | 10/1983 |
| EP | 0 290 327 | 11/1988 |
| JP | 61-13904 | 1/1986 |
| JP | 4-133179 | 5/1992 |
| JP | 7-67721 | 3/1995 |
| JP | 10-233931 | 9/1998 |

* cited by examiner

Primary Examiner—Joe H. Cheng
(74) Attorney, Agent, or Firm—Oblon, Spivak, McClelland, Maier & Nuestadt, P.C.

(57) ABSTRACT

An object of the present invention is to build a simulated image in which a subject's hair is changed to a desired color, and to accurately suggest the hair dye needed to dye the subject's hair from its existing color to the desired color. To achieve this object, the hair color advice system according to the present invention includes (i) an image memory into which image data regarding the subject is input and stored, (ii) a processor that finds the hair area in the input image of the subject and builds a simulated image in which the color of the hair area is changed to any color, and (iii) a monitor 4 on which the input image of the subject and/or the simulated image are displayed.

26 Claims, 5 Drawing Sheets

HAIR COLOR ADVICE SYSTEM

TECHNICAL FIELD

The present invention relates to a method and system by which color of hair is simulated on the hair area of a subject over an image of the subject in order to find what color the subject desires, and identify the hair dye needed to obtain the color.

BACKGROUND ART

Hair dyes and bleach are used to make gray hairs less conspicuous or to dye hair a desired color as a dressing up means. Hair dyes include temporary dyes (color shampoo, color conditioner, color treatment conditioner, etc.) that are easy to apply but the dyed hair retain the color for a short time, semi-permanent dyes (hair manicure, clear-type hair manicure, etc.) that provide a dye effect that can be continuously maintained through penetration of an acidic dye into the interior of the hair, and permanent dyes that achieve an essentially permanent dye effect through oxidation polymerization of the dye in the interior of the hair, and a particular type of hair dye is selected depending on the intended use.

Each of these types of dyes is prepared in numerous color numbers, and each color of dyes is shown by means of printing on the box containing the dye, or by means of sample tresses of dyed hair.

Incidentally, the color of the hair after dyeing is not determined solely by the inherent color of the dye, but affected by the color of the hair before it is dyed. Therefore, even where the same color dye is used, the color of the hair after dyeing differs considerably depending on whether the hair is black, brown or gray before dyeing. In addition, where the same color dye is used, the hair color after dyeing also differs depending on whether the hair is being dyed for the first time using the dye, or whether the hair is being dyed again after the color from a previous dyeing has faded.

Consequently, it is difficult to predict the color that will result from dyeing any person's hair solely from the printing on the box or the sample tresses, and the problem arises that the actual color of the hair after dyeing is different from the color anticipated.

Furthermore, hair dyeing not only changes the color of the hair, but significantly affects the overall appearance of the person whose hair is being dyed. Moreover, it is even more difficult to predict the person's overall appearance after the hair is dyed than it is to predict the color of the person's hair after dyed. As a result, even where the hair color itself turns out as expected, the person may still be displeased with their overall appearance after the dyeing is performed.

DISCLOSURE OF THE INVENTION

An object of the present invention is to accurately suggest the appropriate hair dye to change a person's hair color to the desired color, and to confirm the person's overall appearance after the hair was dyed into the desired color.

The inventors have discovered that, in order to attain this object, it is effective to (1) input the image of the subject (a person) into a memory means of a computer, simulate on a monitor (display screen) the hair color on only the hair area of the input image, and show the simulated image to the subject so that the subject may confirm his or her overall appearance after dyeing, as well as to (2) output the name of the hair dye needed to dye the subject's hair into the same color as the hair color of the simulated image, based on a database that describes references between hair dyes and hair colors before and after dyeing therewith.

The present invention provides a hair color advice system comprising (i) an image memory means into which image data regarding the subject is input and stored, (ii) a processing means that finds the hair area in the input image of the subject and builds a simulated image in which the color of the hair area is changed to any color, and (iii) a monitor (display screen) on which the input image of the subject and/or the simulated image are displayed.

The present invention also provides a hair color advice method (see FIG. 8) comprising (i) a step in which the image data of the subject is input to the image memory means (S800), (ii) a step in which the processing means finds the hair area in the input image of the subject (S802) and builds a simulated image in which the color of the hair area is changed to any color (S804), and (iii) a step in which the input image of the subject and/or the simulated image are displayed on the monitor (display screen) (S806).

In the present invention, the hair dye includes (i) permanent dyes, (ii) semi-permanent dyes such as hair manicures, (iii) temporary dyes such as hair foams, shampoos, conditioners, treatment conditioners, etc. containing coloring agents, and (iv) bleaches, and the hair dyeing includes (i) changing the hair color by means of a hair dye and (ii) bleaching the color of the hair by means of a bleaching agent.

BEST MODE FOR CARRYING OUT THE INVENTION

Figure 1:
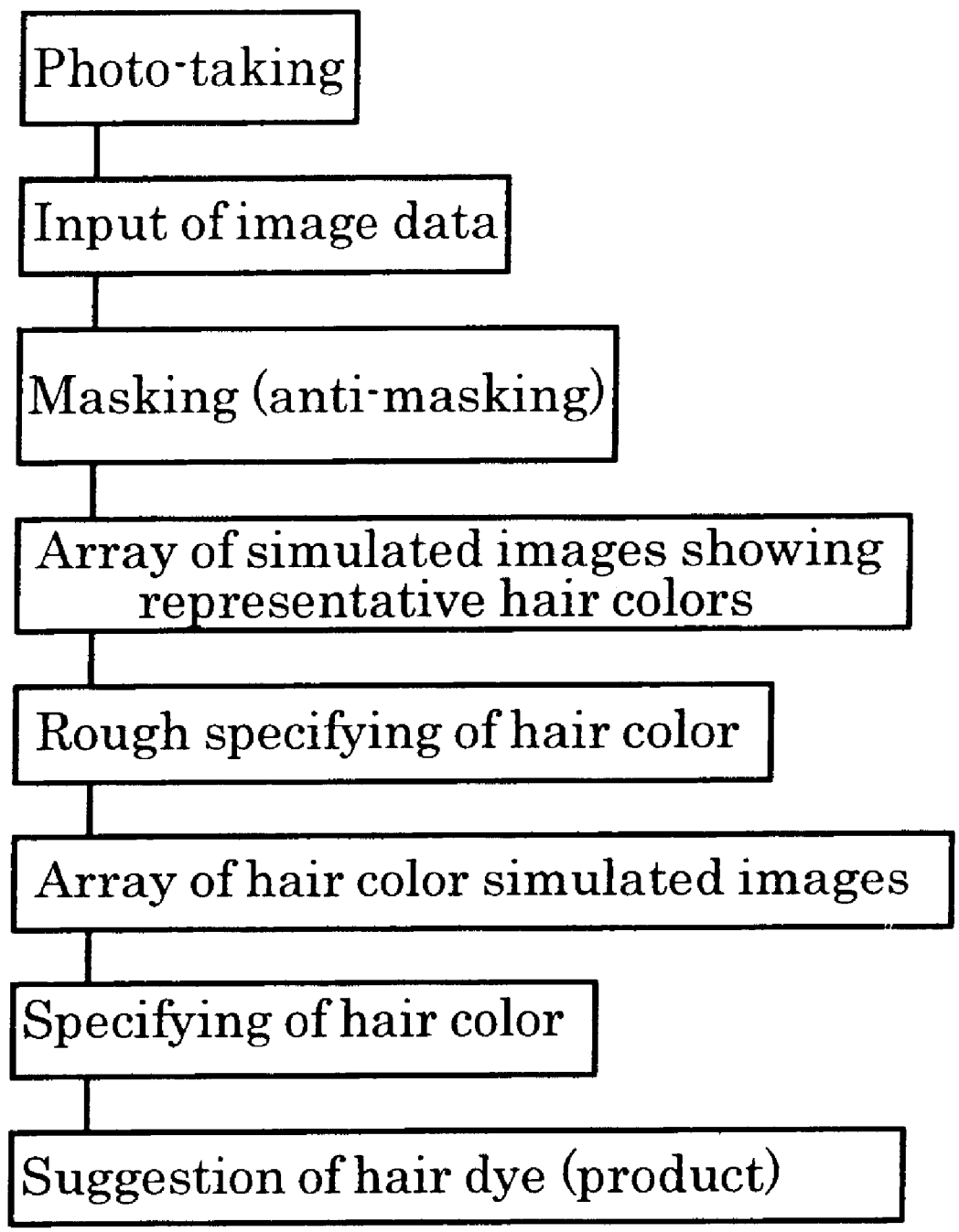
FIG. 1 is a flow chart of the hair color advice method of the present invention.
Figure 2:
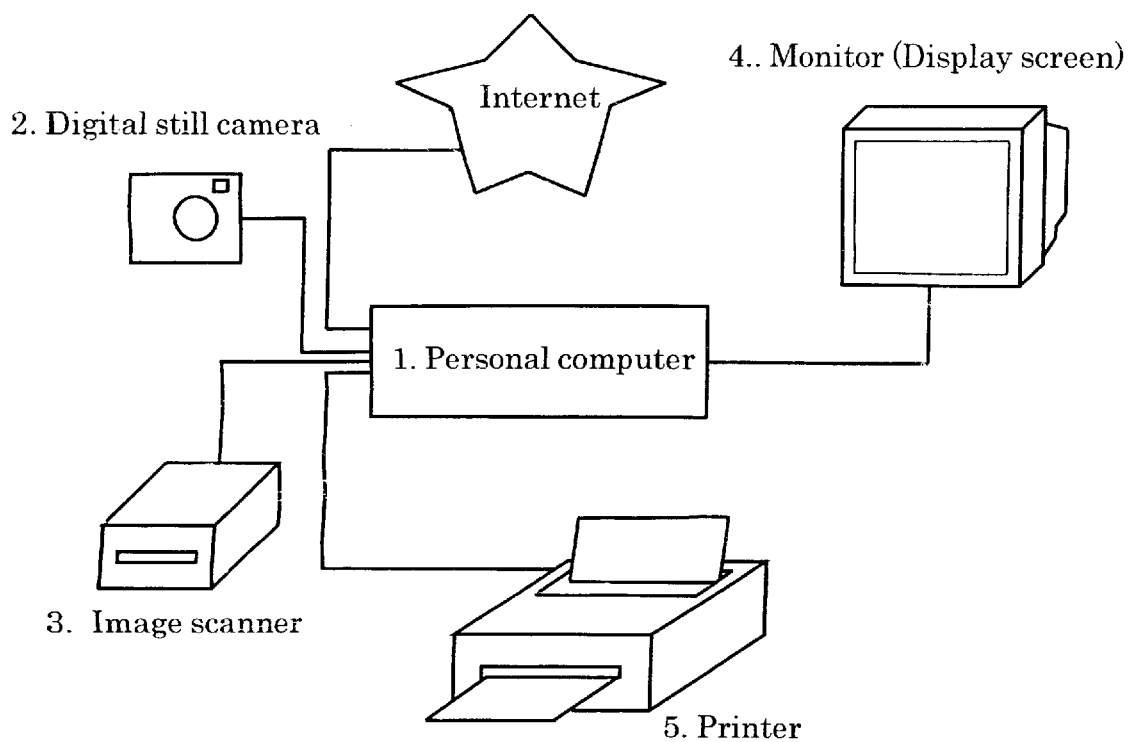
FIG. 2 is a system construction diagram of the hair color advice system of the present invention.

FIG. 1 is a flow chart showing one embodiment of the hair color advice method pertaining to the present invention. FIG. 2 shows an example of the construction of the system that provides this hair color advice method, and includes a personal computer 1 that serves as a memory means into which image data regarding the subject is input and stored and as a processing means that finds the hair area of the subject in the input image and simulates an image with a hair color. Connected to the personal computer 1 are, as an image reading means, a digital still camera 2 that takes a photograph of the subject, an image scanner 3 that reads image data from the photograph of the subject, and a device that can read image data over telecommunications network such as the Internet. A monitor (display screen) 4 and a printer 5 are also connected to the personal computer 1, and are used to show the subject's image data stored in the personal computer 1, as well as associated simulated image data, as required.

In the hair color advice method pertaining to the present invention, first, the subject's image data is input into the personal computer 1 that serves as an image memory means. More specifically, a photograph of the subject is taken of using the digital still camera 2, and this image data is input into and stored in as an image file in the personal computer 1. Alternatively, image data may be taken from the photograph of the subject and input into the personal computer 1 by means of the image scanner 3, or subject's image data previously stored on a desired storage medium may be input into the personal computer 1. It is also acceptable if a face image of the subject is read over telecommunications network such as the Internet and this image data is input into the personal computer 1. The method by which the image data is input into the personal computer 1 is not limited to the methods described above.

To enable the personal computer 1 to accurately find the hair area when building the image simulating for the hair color, it is preferred that the background upon taking a photograph of the subject using the digital still camera 2 or the background color in a photograph of which the subject is taken, is clearly distinguishable from the hair color of the subject. Ordinarily, the preferred background color is blue.

Figure 3:
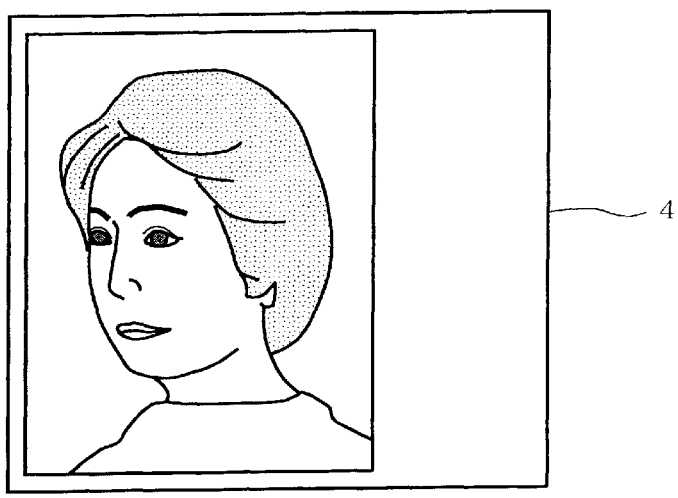
FIG. 3 is a display screen showing the subject image input into a personal computer.

Next, the input image of the subject is output to and shown on the monitor 4. FIG. 3 shows the image of the subject shown on the monitor 4. This step allows the subject to confirm his or her own input image into the personal computer 1.

In the present invention, the personal computer 1 is given also as a processing means which has a function to distinguish the hair area in the input image of the subject. This function renders unnecessary the complex operation that the operator of the personal computer uses a mouse to cut out the hair area that comprises the subject of the simulation. This distinguishing function may be enabled in the personal computer 1 by incorporating therein a software program that distinguishes the hair area from the non-hair areas based on such parameters as their brightness and hue, as well as the continuousness of the changes in such parameters or the like.

Where the hair area in the input image of the subject is distinguished by means of the personal computer 1, it may occur that, depending on the hair color or other factors, the actual hair area is not accurately distinguished from the non-hair areas. Therefore, it is desirable that the areas that are not included in the actual hair area but may be identified by the personal computer 1 as a part of the hair area because they are similar to the actual hair area in terms of brightness, hue and the like, and may be subjected to hair color simulation together with the hair area, be designated in advance so that hair color simulation is not carried out for the designated areas. Therefore, it is preferred that the personal computer 1 has a masking function by which certain areas of the input image of the subject are designated as non-simulation areas by the operator of the personal computer.

Conversely, where as a result of reflection during photo exposure or the like, the input image of the subject is whited out in part in the hair area, there is a risk that the personal computer 1 will distinguish any whited-out part of the actual hair area as a non-hair area, and will eliminate that part as a subject of the simulation. To solve this problem, it is preferred that the hair color simulation is performed with respect to a pre-designated area regardless of the results of the hair area determination carried out by the personal computer 1. Therefore, it is preferred that the personal computer 1 has an anti-masking function by which an area of the subject's input image specified by the operator of the personal computer is deemed a hair color simulation area.

Figure 4:
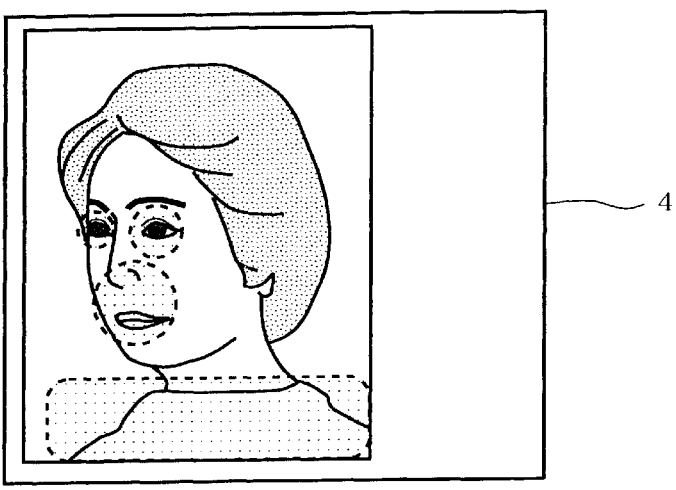
FIG. 4 is a drawing to explain masking.

As a specific example of this masking step, where the subject has black hair, for example, the personal computer operator specifies such dark areas as the eyes, the nostrils and mouth, clothing or the like, as indicated by the areas enclosed with dashed lines in FIG. 4, and instructs that masking is performed with respect to these areas. The personal computer operator may specify based on the preference of the subject, whether the eyebrows will be simulated together with the hair or not. Where the hair is light brown or blonde, like that of a European people, the personal computer operator specifies on the display screen and performs masking with respect to bright areas such as the face, clothing, etc. In this case as well, eyebrows are handled in the same manner as in the situation in which the hair was dark.

To enable the personal computer 1 to accurately distinguish between hair areas and non-hair areas in the subject's input image, it is preferred that the personal computer 1 is able to individually set the parameters required to differentiate between hair and non-hair areas in accordance with the image background color, the hair color, etc.

After the masking step or the anti-masking step is performed, the hair color desired by the subject is specified on the personal computer, and a hair color simulated image is built and displayed on the monitor 4 in which the hair area (more precisely, the hair area found by the personal computer 1, or the corrected areas comprising the hair area and the areas designated by means of the masking or anti-masking) in the image of the subject is changed to the desired hair color.

For the method of building the simulated image, it is preferred that the color of the hair area in the input image is properly reflected in the image input into the computer, and that a color having a prescribed hue or brightness is overlaid onto it. More specifically, it is preferred that a simulation software program having these functions is incorporated into the personal computer 1.

Because the simulated image displayed on the monitor 4 represents the initial image of the subject that was incorporated into the personal computer 1, with only the hair area changed to the desired color, the subject can not only confirm the hair color after dyeing by means of this simulated image, but can get a feel for his or her overall appearance after dyeing.

Figure 5:
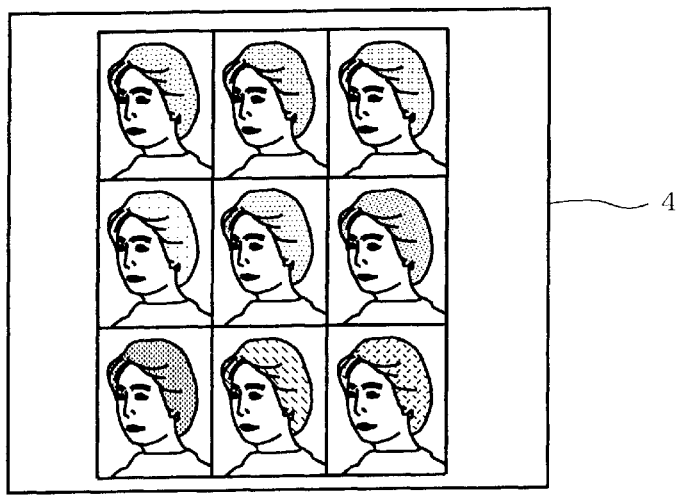
FIG. 5 is a display screen showing an array of simulated images.

In the step in which the subject specifies a hair color, it is preferred that an array of simulated images in which the subject's hair is dyed to various representative colors are first displayed on the monitor 4 (see FIG. 5), whereupon the subject may generally indicate the desired hair color from among the simulated images displayed. When this is performed, the subject's preference regarding the permanence of the dye, i.e., the subject preference for a temporary dye or a semi-permanent dye, as well as the subject's prior history of dyeing, the existence of any allergic reactions to chemicals of the subject, etc., may be input to the personal computer 1, if necessary, so that this information is reflected when the dye corresponding to the desired hair color is subsequently output from the personal computer 1.

Figure 6:
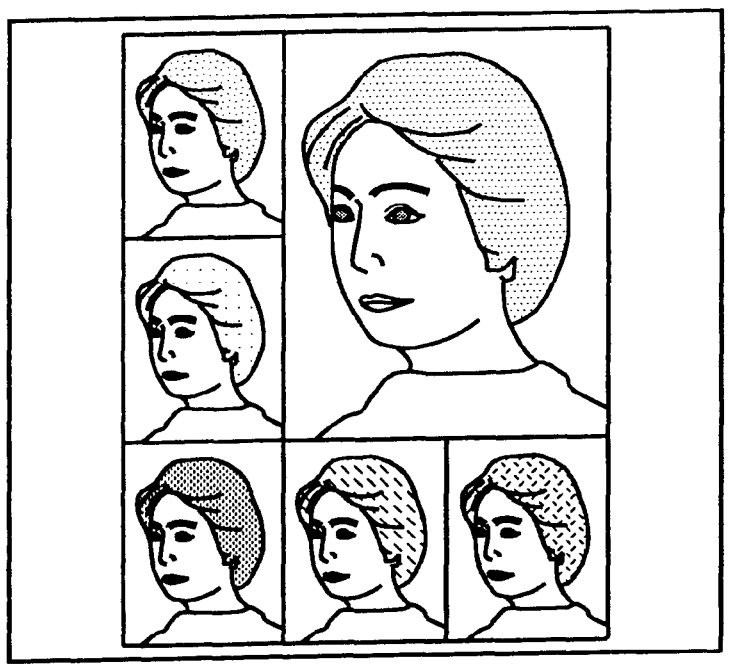
FIG. 6 is a display screen showing a simulated image of a specified hair color.

It is preferred that after the hair color is roughly specified, an array of simulated images is displayed in which the hair colors are changed by degrees into colors nearby the desired color, so that the subject may once again specify the desired hair color. It is furthermore preferred that the simulated image of the hair color thus specified by the subject is displayed in an enlarged fashion on the monitor 4 (see FIG. 6).

The specifying of the hair color and the display of he simulated images may be performed repeatedly until the subject is satisfied.

After the hair color desired by the subject is confirmed, it is preferred that a hair dye suggesting step is conducted in which, based on a database in which accumulated is information on hair dyes and hair colors before and after dyeing therewith, the personal computer 1 outputs the dye necessary to dye the subject's hair into the color specified by the subject; more specifically the personal computer 1 displays on the monitor 4 the type, color number, product name, etc., of the dye necessary to dye the subject's hair into the color specified by the subject, and thereafter output these information to the printer 5. The contents of these information may be transmitted to the subject via telecommunications network such as the Internet, or may be sent to the subject via direct mail.

Figure 7:
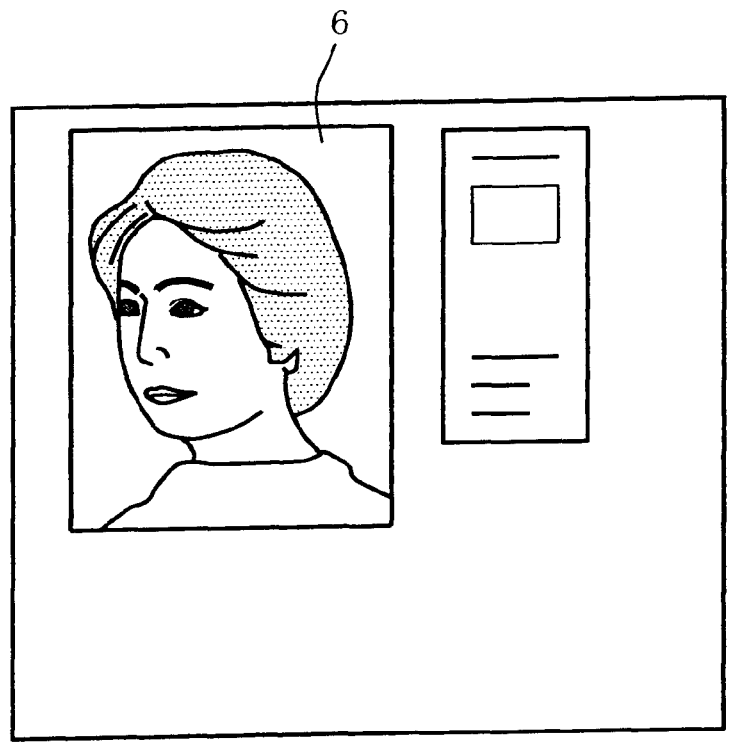
FIG. 7 is a display screen showing a hair dye suggested.
Figure 8:
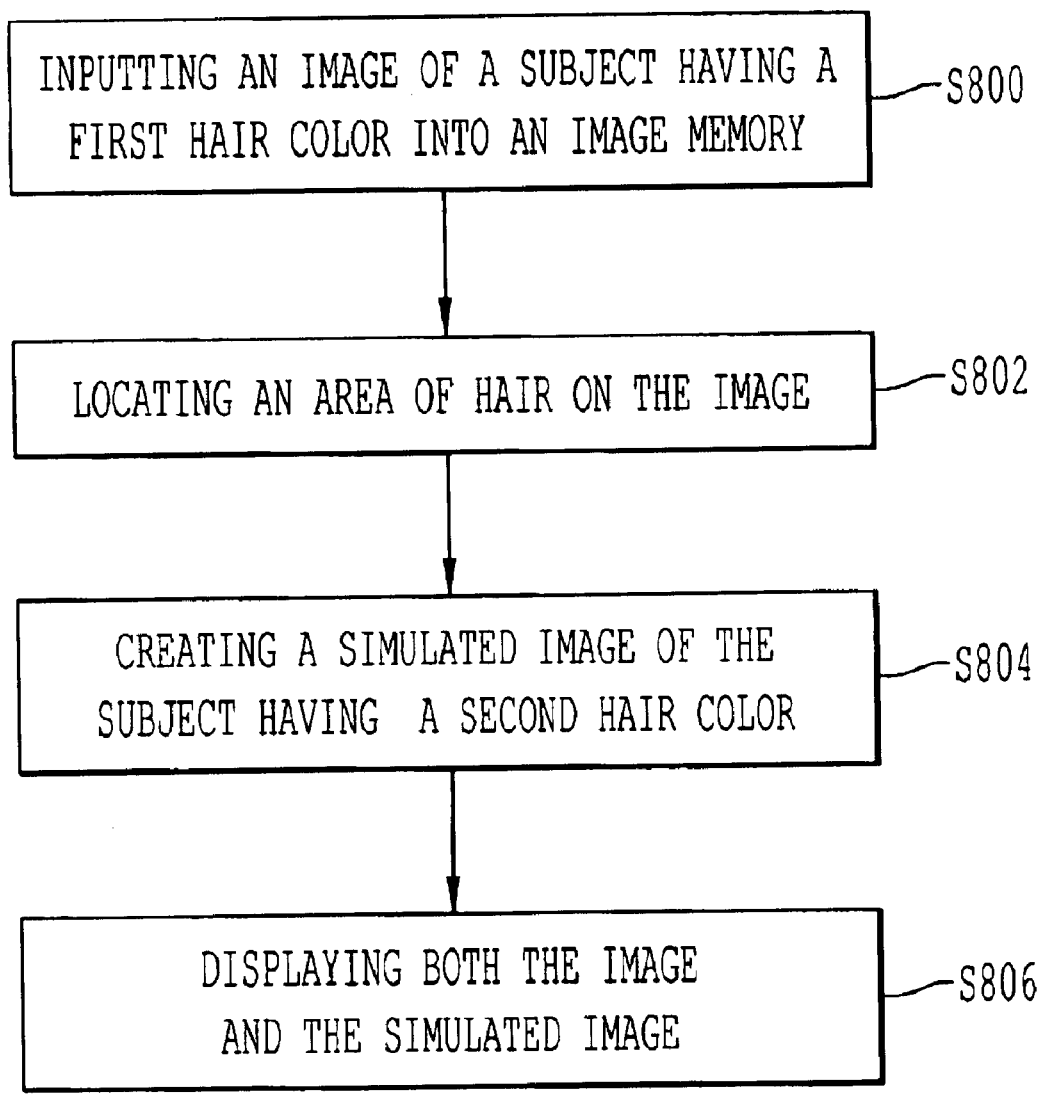
FIG. 8 is the method steps of the hair color advice method of the present invention.

It is furthermore preferred that the hair color simulated image and the actual product image 6 are displayed on the hair dye output screen (see FIG. 7). In this way, the subjects may know with certainty the hair dye needed to achieve the desired hair color for his or her own hair.

INDUSTRIAL APPLICABILITY

As described above, because the present invention enables the subjects to know their appearances as the simulated images when their hairs are dyed into the desired colors, the subjects can confirm not only their hair colors after dyeing, but also their entire overall impressions. In addition, by means of the present invention, the hair dyes needed to dye the subject's present colors into the desired colors may be reliably identified as well.

What is claimed is:

1. A hair color advice system, comprising:
   an image memory configured to receive and store an image of a subject having a first hair color;
   a processor configured to locate an area of hair on the image and to create a simulated image of the subject having a second hair color; and
   a monitor configured to display both the image and the simulated image.

2. The hair color advice system according to claim 1, further including an image reading apparatus configured to read data of the image.

3. The hair color advice system according to claim 1, wherein the processor is configured to perform an anti-masking function for determining the area of hair and a masking function for determining a second area that is not the area of hair.

4. The hair color advice system according to claim 1, wherein the processor is configured to output an appropriate dye for dyeing hair of the subject based at least in part on the simulated image.

5. The hair color advice system according to claim 4, wherein the processor is configured to select the appropriate dye from a database, the database including information for a plurality of dyes.

6. The hair color advice system according to claim 5, wherein the information includes characteristics of the plurality of dyes before and after application.

7. The hair color advice system according to claim 1, wherein the simulated image is an array of simulated images.

8. A hair color advice method, comprising:
   inputting an image of a subject having a first hair color into an image memory;
   locating an area of hair on the image;
   creating a simulated image of the subject having a second hair color; and
   displaying both the image and the simulated image.

9. The method according to claim 8, further comprising:
   performing an anti-masking function for determining the area of hair and a masking function for determining a second area that is not the area of hair.

10. The method according to claim 8, further comprising:
    suggesting an appropriate dye for dyeing hair of the subject based at least in part on the simulated image.

11. The method according to claim 10, wherein the suggesting step includes selecting the appropriate dye from a database, the database including information for a plurality of dyes.

12. The method according to claim 11, wherein the information includes characteristics of the plurality of dyes before and after application.

13. The method according to claim 8, wherein the simulated image is an array of simulated images.

14. A hair color advice system, comprising:
    an image memory configured to receive and store an image of a subject having a first hair color;
    a processor configured to locate an area of hair on the image and to create a simulated image of the subject having a second hair color on the area of hair; and
    a monitor configured to display at least one of the image and the simulated image, wherein the area of hair includes an eyebrow.

15. The hair color advice system according to claim 14, further including an image reading apparatus configured to read data of the image.

16. The hair color advice system according to claim 14, wherein the processor is configured to perform an anti-masking function for determining the area of hair and a masking function for determining a second area that is not the area of hair.

17. The hair color advice system according to claim 14, wherein the processor is configured to output an appropriate dye for dyeing hair of the subject based at least in part on the simulated image.

18. The hair color advice system according to claim 17, wherein the processor is configured to select the appropriate dye from a database, the database including information for a plurality of dyes.

19. The hair color advice system according to claim 18, wherein the information includes characteristics of the plurality of dyes before and after application.

20. The method according to claim 14, wherein the simulated image is an array of simulated images.

21. A hair color advice method, comprising:
    inputting an image of a subject having a first hair color into an image memory;

locating an area of hair on the image;

creating a simulated image of the subject having a second hair color; and displaying at least one of the simulated image and the image, wherein the area of hair includes an eyebrow.

22. The method according to claim 21, further comprising:

performing an anti-masking function for determining the area of hair and a masking function for determining a second area that is not the area of hair.

23. The method according to claim 21, further comprising:

suggesting an appropriate dye for dyeing hair of the subject based at least in part on the simulated image.

24. The method according to claim 23, wherein the suggesting step includes selecting the appropriate dye from a database, the database including information for a plurality of dyes.

25. The method according to claim 24, wherein the information includes characteristics of the plurality of dyes before and after application.

26. The method according to claim 21, wherein the simulated image is an array of simulated images.

* * * * *